United States Patent [19]

McMahan

[11] Patent Number: 5,778,891
[45] Date of Patent: Jul. 14, 1998

[54] SURGICAL DRAPE

[75] Inventor: Dorothy R. McMahan, Titus, Ala.

[73] Assignees: Missy D. Margolis, Framingham, Mass.; Patrick N. Trotter, Prattville, Ala.

[21] Appl. No.: 917,090

[22] Filed: Aug. 25, 1997

[51] Int. Cl.$^6$ .................................................. A61B 19/00
[52] U.S. Cl. ................................................ 128/849; 128/853
[58] Field of Search .................................. 128/849–856

[56] References Cited

U.S. PATENT DOCUMENTS

| | | | |
|---|---|---|---|
| 5,161,544 | 11/1992 | Morris | 128/853 |
| 5,445,165 | 8/1995 | Fenwick | 128/853 |
| 5,471,999 | 12/1995 | Mills | 128/853 |
| 5,592,952 | 1/1997 | Bohn | 128/853 |

*Primary Examiner*—Michael A. Brown
*Attorney, Agent, or Firm*—John E. Toupal; Harold G. Jarcho

[57] ABSTRACT

A surgical drape including a flexible bottom sheet having a lower surface of given area for placement on a patient and an upper surface for facing away from the patient, the bottom sheet defining a bottom fenestration of given size for accommodating a surgical procedure. Also included is a flexible top sheet detachably secured to the upper surface of the bottom sheet and covering the bottom fenestration. The top sheet has bottom and top surfaces of predetermined area less than the given area and defines a top fenestration of predetermined size smaller than the given size and aligned with bottom fenestration. A securement mechanism is provided for securing the top sheet around a body appendage after detachment of the top sheet from the bottom sheet. The securement mechanism improves use flexibility of the surgical drape.

20 Claims, 4 Drawing Sheets

5,778,891

SURGICAL DRAPE

BACKGROUND OF THE INVENTION

The present invention relates generally to surgical drapes and, more particularly, to surgical drapes with multiple components.

A various assortment of drapes have been proposed for surgical procedures, during which the drapes are used to cover the body of a patient and maintain a sterile barrier around the operative site while the procedure is performed through a fenestration in the drape. Typically, such drapes have been provided with fenestrations of a predetermined size for use in a particular surgical procedure depending upon the size and location of the surgical site. Accordingly, an excessive number of drapes are required, and drapes must sometimes be replaced or cut pursuant to related procedures. For example, procedures on children and adults require fenestrations of different size. Accordingly, it has been necessary for hospitals to maintain a stock of different drapes for performing the different procedures. Alternatively, the fenestration of a drape designed for a smaller surgical procedure must be cut to enlarge the fenestration for an expanded surgical procedure, which has been time consuming and inconvenient for the operating room team, as well as increasing the likelihood of contamination of the drape.

Disclosed in U.S. Pat. No. 4,024,862 is an improved surgical drape usable selectively for surgical procedures involving sites of various size. The disclosed surgical drape fails, however, to fully satisfy certain surgical needs.

The object of this invention, therefore, is to provide an improved surgical drape which can be used selectively for a wide variety of surgical procedures.

SUMMARY OF THE INVENTION

The invention is a surgical drape including a flexible bottom sheet having a lower surface of given area for placement on a patient and an upper surface for facing away from the patient, the bottom sheet defining a bottom fenestration of given size for accommodating a surgical procedure. Also included is a flexible top sheet detachably secured to the upper surface of the bottom sheet and covering the bottom fenestration. The top sheet has bottom and top surfaces of predetermined area less than the given area and defines a top fenestration of predetermined size smaller than the given size and aligned with bottom fenestration. A securement mechanism is provided for securing the top sheet around a body appendage after detachment of the top sheet from the bottom sheet. The securement mechanism improves use flexibility of the surgical drape.

According to one feature of the invention, the securement strap includes a plurality of straps attached to spaced apart locations on the top surface and arranged to accommodate tying the top sheet around a body appendage. The straps facilitate independent use of the top sheet during appropriate surgical procedures.

According to another feature of the invention, the drape also includes a flexible auxiliary sheet detachably secured to the top surface of the top sheet and covering the top fenestration. The auxiliary sheet has upper and lower surfaces each of an area less than the predetermined area and defines an auxiliary fenestration of a size smaller than the predetermined size and aligned with the top fenestration. An attachment mechanism is provided also for securing the auxiliary sheet to a body appendage after detachment of the auxiliary sheet from the top sheet. Use flexibility of the surgical drape is enhanced further by the auxiliary sheet and attachment mechanism therefor.

According to an additional feature of the invention, the surgical drape includes an elongated absorbent pad removably secured to a marginal portion of the upper surface of the bottom sheet. During a surgical procedure, the absorbent pad can be strategically positioned to collect fluid runoff.

According to a further feature of the invention, the bottom sheet has a peripheral hem and the surgical drape includes a plurality of weights retained in spaced apart locations within the hem. The weights retain the surgical drape in a selected position during a surgical procedure.

According to still another feature of the invention, the bottom sheet is a given color, the top sheet is a predetermined color different than the given color, and the auxiliary sheet is another color different than either of the given and predetermined colors. The different colors simplify visual identification of the top and auxiliary sheets prior to selective removal thereof.

BRIEF DESCRIPTION OF THE DRAWINGS

These and other objects and features of the invention will become more apparent upon a perusal of the following description taken in conjunction with the accompanying drawings wherein:

In FIGS. 2–6, strap portions of the surgical drapes are omitted to preserve clarity.

DESCRIPTION OF THE PREFERRED EMBODIMENT

Figure 1:
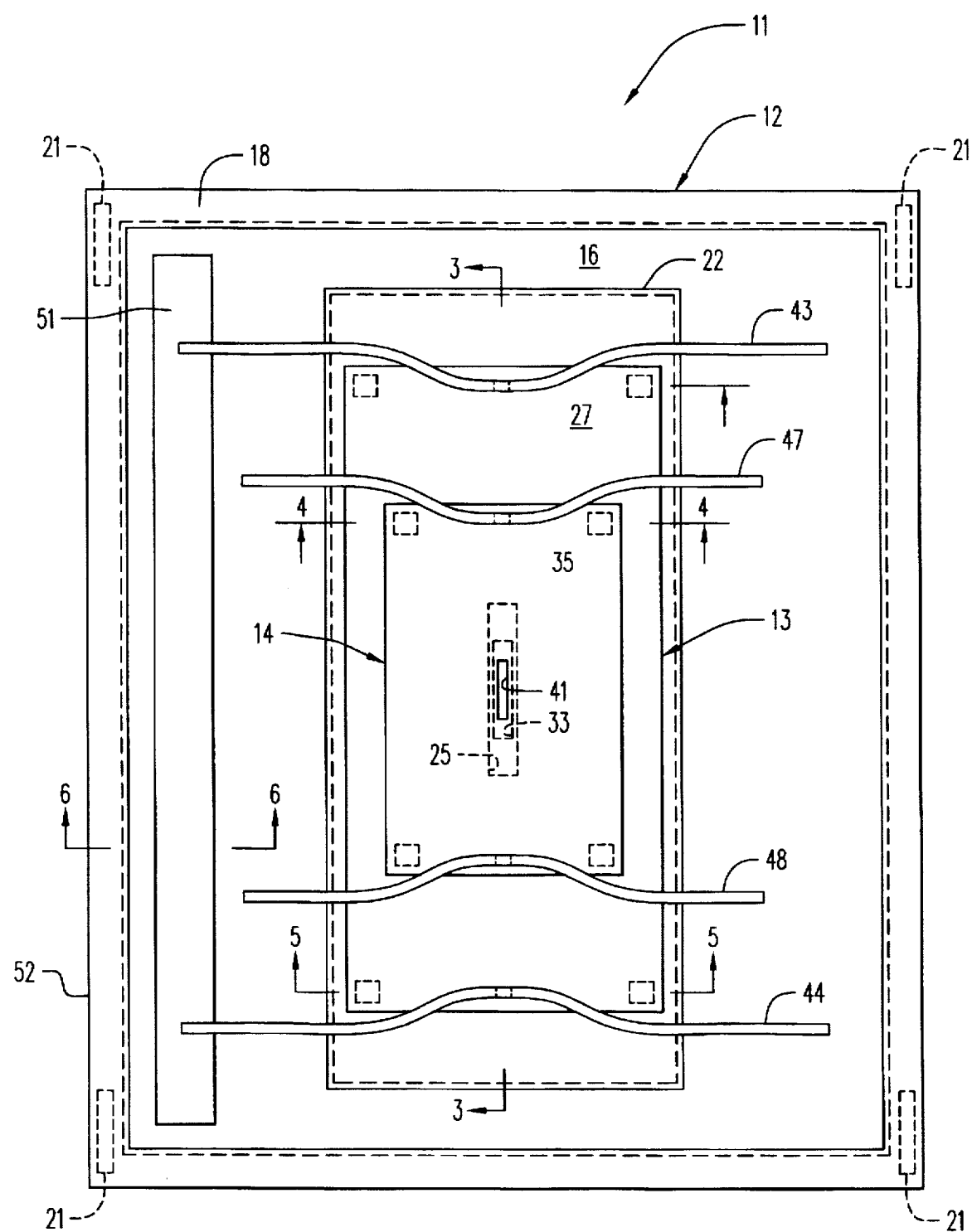
FIG. 1 is a top plan view of a surgical drape according to the invention.
Figure 2:
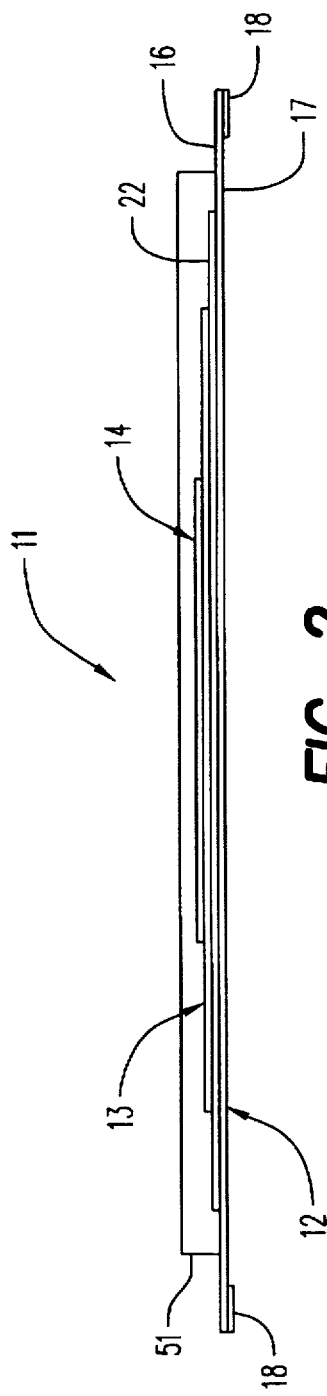
FIG. 2 is a right elevational view of the surgical drape shown in FIG. 1.
Figure 3:
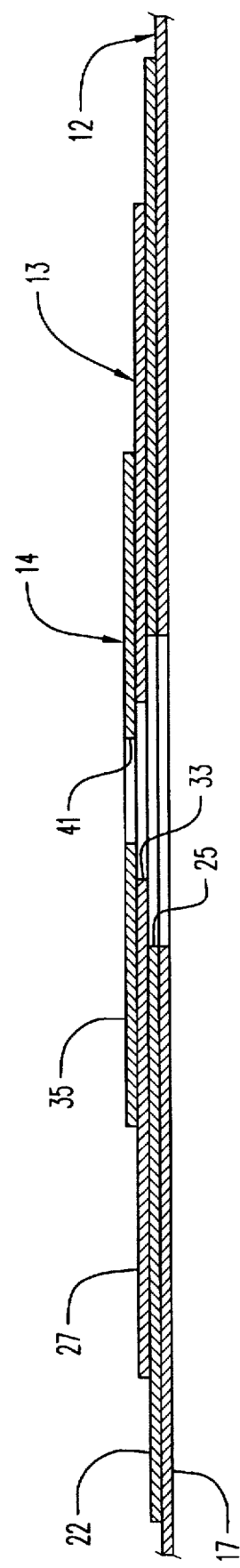
FIG. 3 is a partial cross sectional view taken along lines 3—3 of FIG. 1.

A surgical drape 11 includes a flexible bottom sheet 12, a flexible top sheet 13 detachably secured to the bottom sheet 12 and a flexible auxiliary sheet 14 detachably secured to the top sheet 13. The bottom sheet 12 has, respectively, upper and lower surfaces 16, 17 of a given area and a rectangular peripheral hem 18. Retained in each spaced apart corner location of the peripheral hem is a weight 21. A flexible panel 22 is secured, for example with stitching, to a central portion of the upper surface 16 of the bottom sheet 12. The panel 22 strengthens a central portion of the bottom sheet 12. Extending through the bottom sheet 12 and the flexible panel 22 is a bottom fenestration 25 of given size.

Figure 5:
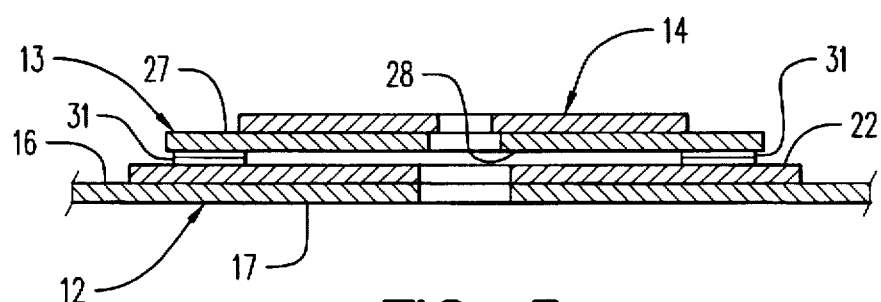
FIG. 5 is a cross sectional view taken along lines 5—5 of FIG. 1.

The flexible top sheet 13 has, respectively, rectangular top and bottom surfaces 27, 28 of a predetermined area less than the given area of the upper and lower surfaces 16, 17 of the bottom sheet 12. Detachably securing the top sheet 13 to the bottom sheet 12 are engaged pairs 31 of compatible Velcro pads (FIG. 5) attached, respectively, to the upper surface of the bottom sheet 12 and the bottom surface 28 of the top sheet 13. The pairs 31 of securing pads are located at corner portions of the bottom surface 28 of the top sheet 13. Extending through a central portion of the top sheet 13 is a top fenestration 33 of a predetermined size smaller than the given size of the bottom fenestration 25 and aligned therewith.

Figure 4:
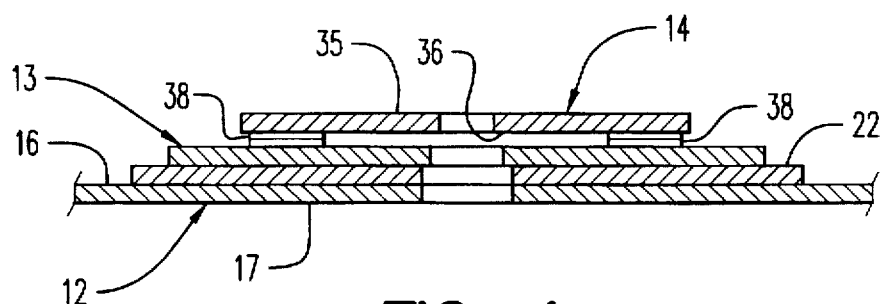
FIG. 4 is a cross sectional view taken along lines 4—4 of FIG. 1.

The flexible auxiliary sheet 14 has, respectively, upper and lower surfaces 35, 36 of area less than the predetermined area of the top and bottom surfaces 27, 28 of the top sheet 13. Detachably securing the top auxiliary sheet 14 to the top sheet 13 are engaged pairs 38 of Velcro pads (FIG. 4) attached, respectively, to the top surface of the top sheet 13 and the lower surface 36 of the auxiliary sheet 14. The Velcro pad pairs 38 are located at corner portions of the lower surface 36 of the auxiliary sheet 14. Extending through a central portion of the auxiliary sheet 14 and aligned with the bottom fenestration 25 and the top fenestration 33 is an auxiliary fenestration 41 having a size smaller than the top fenestration 33.

A pair of top securement straps 43, 44 (FIG. 1) are attached to the top sheet 13 and a pair of auxiliary securement straps 47, 48 are secured to the auxiliary sheet 14. The top securement straps 43, 44 are secured, as by stitching, to spaced apart locations adjacent to opposite edges of the top surface 27 of the top sheet 13. Similarly, the auxiliary straps 47, 48 are attached to spaced apart locations adjacent to opposite edges of the upper surface 35 of the auxiliary sheet 14.

Figure 6:
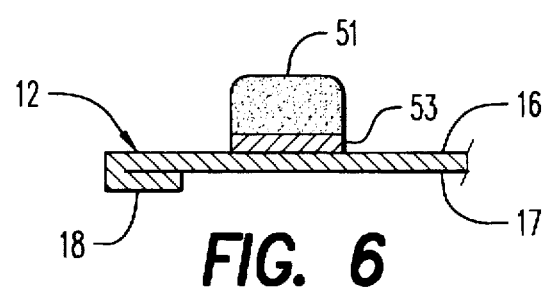
FIG. 6 is a partial cross sectional view taken along lines 6—6 of FIG. 1.

An elongated flexible pad 51 is positioned on the upper surface 16 of the bottom sheet 12 adjacent to and substantially coextensive with one edge 52 thereof. Removably securing the absorbent pad 51 to the upper surface 16 of the bottom sheet 12 is a suitable adhesive 53 (FIG. 6). The absorbent pad 51 preferably is formed of absorbent material of the type used for conventional sanitary napkins.

In use, one or both of the top and auxiliary sheets 13 or 14 may be removed from the drape 11 in order to define different sized fenestrations for separate surgical procedures. Thus, for a surgical procedure requiring a relatively small operative site, the surgical procedure may be performed through the fenestration 41 of the auxiliary sheet 14. If a moderate sized fenestration is needed for the surgical procedure, the auxiliary sheet 14 may be removed from the sheet 13 in order to expose the fenestration 33 through which the surgical procedure is performed. In the event that a relatively large fenestration is required for the operation, the top sheet 13 is also removed from the drape 11 in order to expose the fenestration 25 through which the expanded surgical procedure may be performed. Of course, any number of frame sheets having fenestrations of varying sizes may be overlapped in a manner as described in connection with the drape 11 of FIGS. 1–6. To facilitate selective removal of the top sheet 13 or auxiliary sheet 14, different colors are preferably employed for each of the bottom sheet 12 the top sheet 13 and the auxiliary sheet 14. The use of contrasting colors simplifies visual location of the top and auxiliary sheets 13, 14 prior to detachment thereof.

Figure 7:
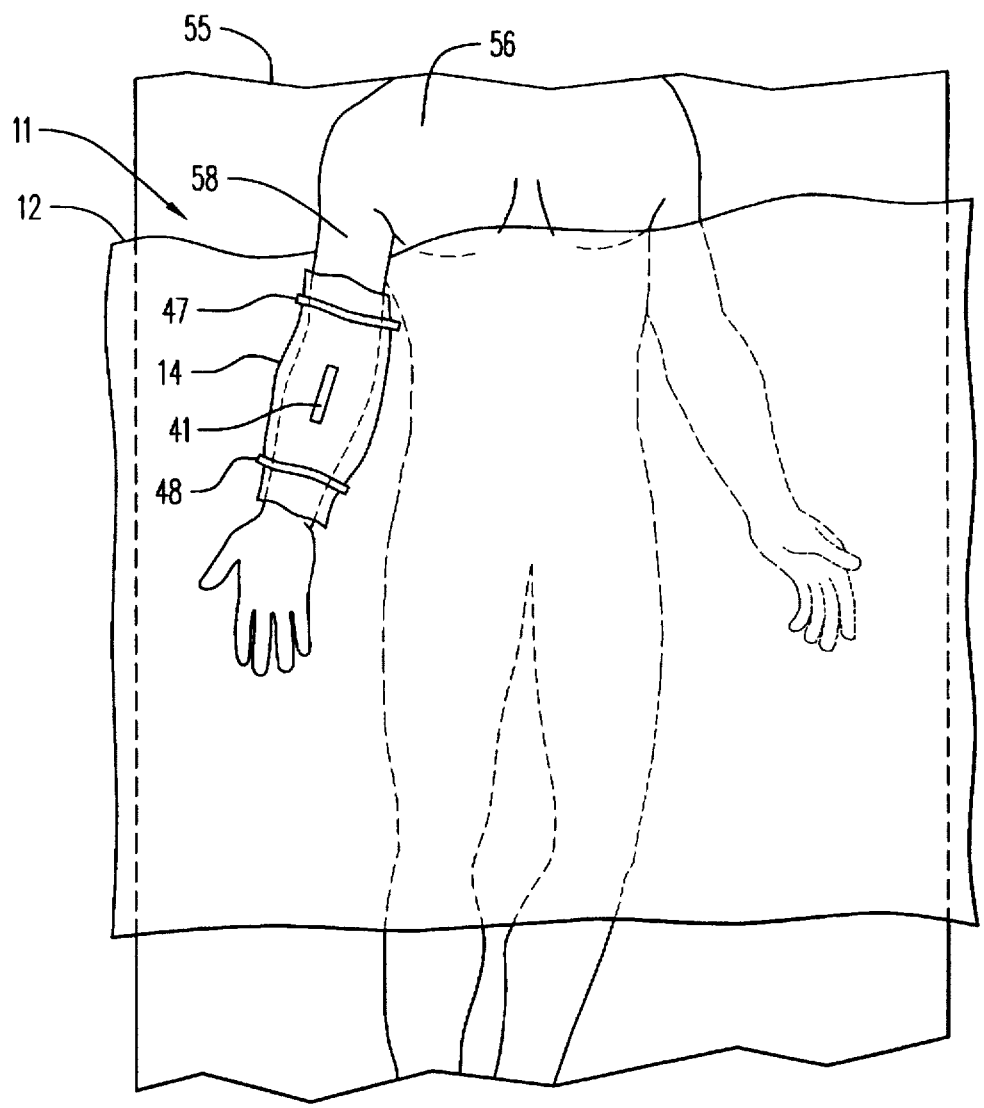
FIG. 7 is a pictorial view showing use of a component of the surgical drape shown in FIGS. 1–6.

During preferred use, the surgical drape 11 is placed strategically on a patient with the bottom sheet 12 positioned such that the absorbent pad 51 is aligned horizontally below the surgical site as depicted in FIG. 7. Consequently, surgically produced fluid runoff is absorbed by the pad 51 to thereby prevent soiling of adjacent surfaces. After completion of the surgical process, the absorbent pad 51 is removed from the bottom sheet 12 and disposed as biological waste. Prior to reuse of the surgical drape 11 and after washing thereof, a replacement absorbent pad 51 again is secured to the edge portion 52 of the bottom sheet 12.

Illustrated in FIG. 7 is an alternative use of the surgical drape 11. In this operational mode, the bottom sheet 12 is draped over appropriate portions of an operating table 55 and patient 56 and under a body appendage, e.g. an arm 58, on which surgery is to be performed. Next, either the top sheet 13 or the auxiliary sheet 14 is selected in accordance with the size of the operative site on which surgery is to be performed. Assuming in this case that the auxiliary sheet 14 is selected, it then is wrapped around the appendage with the fenestration 41 therein aligned with the operative site and the straps 47, 48 are tied to secure the sheet in position. Having been secured by the straps 47, 48, the auxiliary sheet 14 remains in the desired position despite possible movement of the patient 56. In addition, the bottom sheet 12 establishes a sterile field for supporting instruments, sutures or other paraphernalia used in the operative procedure.

Obviously, many modifications and variations of the present invention are possible in light of the above teachings. For example, conventional securement mechanisms other than the disclosed Velcro pairs 31, 38 or tie straps 43, 44, 47 and 48 could be employed. Also, surgical drape packages can be provided with various sized top and auxiliary sheets provided that the mechanisms used for securement are standardized. It will be further appreciated that the drape 11 could be produced in disposable form and that sheet shapes other than the rectangular types disclosed could be used depending on applications of use. It is to be understood, therefore, that the invention can be practiced otherwise than as specifically described.

What is claimed is:

1. A surgical drape comprising:
   a flexible bottom sheet having a lower surface of given area for placement on a patient and an upper surface for facing away from the patient, said bottom sheet defining a bottom fenestration of given size for accommodating a surgical procedure;
   a flexible top sheet detachably secured to said upper surface of said bottom sheet and covering said bottom fenestration, said top sheet having bottom and top surfaces of predetermined area less than said given area and defining a top fenestration of predetermined size smaller than said given size and aligned with bottom fenestration; and
   securement means for securing said top sheet around a body appendage after detachment of said top sheet from said bottom sheet.

2. A surgical drape according to claim 1 wherein said securement means comprises strap means for securing said top sheet around the body appendage.

3. A surgical drape according to claim 2 wherein said strap means comprises a plurality of straps attached to spaced apart locations on said top surface.

4. A surgical drape according to claim 3 wherein said straps are arranged to accommodate tying said top sheet around the body appendage.

5. A surgical drape according to claim 1 including a flexible auxiliary sheet detachably secured to said top surface of said top sheet and covering said top fenestration, said auxiliary sheet having upper and lower surfaces each of an area less than said predetermined area and defining an auxiliary fenestration of a size smaller than said predetermined size and aligned with said top fenestration; and attachment means for securing said auxiliary sheet to a body appendage after detachment of said auxiliary sheet from said top sheet.

6. A surgical drape according to claim 5 wherein said securement means comprises strap means for securing said top sheet around the body appendage, and said attachment means comprises strap means for securing said auxiliary sheet around a body appendage.

7. A surgical drape according to claim 6 wherein each said strap means comprises a plurality of straps attached to spaced apart locations on each of said top and auxiliary sheets.

8. A surgical drape according to claim 7 wherein said straps are arranged to accommodate tying of said top and auxiliary sheets around the body appendage.

9. A surgical drape according to claim 1 including an elongated absorbent pad removably secured to a marginal portion of said upper surface of said bottom sheet.

10. A surgical drape according to claim 9 wherein said securement means comprises strap means for securing said top sheet around the body appendage.

11. A surgical drape according to claim 10 wherein said strap means comprises a plurality of straps attached to spaced apart locations on said top surface.

12. A surgical drape according to claim 11 wherein said straps are arranged to accommodate tying said top sheet around the body appendage.

13. A surgical drape according to claim 12 including a flexible auxiliary sheet detachably secured to said top surface of said top sheet and covering said top fenestration, said auxiliary sheet having upper and lower surfaces each of an area less than said predetermined area and defining an auxiliary fenestration of a size smaller than said predetermined size and aligned with said top fenestration; and attachment means for securing said auxiliary sheet to a body appendage after detachment of said auxiliary sheet from said top sheet.

14. A surgical drape according to claim 13 wherein said securement means comprises strap means for securing said top sheet around the body appendage, and said attachment means comprises strap means for securing said auxiliary sheet around a body appendage.

15. A surgical drape according to claim 14 wherein each said strap means comprises a plurality of straps attached to spaced apart locations on each of said top and auxiliary sheets.

16. A surgical drape according to claim 15 wherein said straps are arranged to accommodate tying of said top and auxiliary sheets around the body appendage.

17. A surgical drape according to claim 1 wherein said bottom sheet has a peripheral hem, and including a plurality of weights retained in spaced apart locations within said hem.

18. A surgical drape according to claim 5 wherein said bottom sheet is a given color, said top sheet is a predetermined color different than said given color, and said auxiliary sheet is another color different than either of said given and predetermined colors.

19. A surgical drape comprising:
a flexible bottom sheet having a lower surface of given area for placement on a patient and an upper surface for facing away from the patient, said bottom sheet defining a bottom fenestration of given size for accommodating a surgical procedure;
a flexible top sheet detachably secured to said upper surface of said bottom sheet and covering said bottom fenestration, said top sheet having bottom and top surfaces of predetermined area less than said given area and defining a top fenestration of predetermined size smaller than said given size and aligned with bottom fenestration; and
an elongated absorbent pad secured to a marginal portion of said upper surface of said bottom sheet.

20. A surgical drape comprising:
a flexible bottom sheet having a lower surface of given area for placement on a patient and an upper surface for facing away from the patient, said bottom sheet defining a bottom fenestration of given size for accommodating a surgical procedure;
a flexible top sheet detachably secured to said upper surface of said bottom sheet and covering said bottom fenestration, said top sheet having bottom and top surfaces of predetermined area less than said given area and defining a top fenestration of predetermined size smaller than said given size and aligned with said bottom fenestration; and
a plurality of weights retained in spaced apart locations about the periphery of said bottom sheet.

* * * * *